United States Patent [19]

Kuroishi et al.

[11] Patent Number: 4,557,601
[45] Date of Patent: Dec. 10, 1985

[54] ELIMINATION OF GHOST COMPONENT IN FLOW INJECTION ANALYSIS METHOD

[75] Inventors: Tadafumi Kuroishi; Kazuo Yasuda, both of Katsuta, Japan

[73] Assignee: Hitachi, Ltd., Tokyo, Japan

[21] Appl. No.: 421,377

[22] Filed: Sep. 22, 1982

[30] Foreign Application Priority Data

Sep. 24, 1981 [JP] Japan ................................ 56-149522

[51] Int. Cl.$^4$ .............................................. G01J 3/42
[52] U.S. Cl. .................................... 356/320; 356/326
[58] Field of Search ............... 356/319, 320, 326, 328, 356/410, 411

[56] References Cited

U.S. PATENT DOCUMENTS 3,966,323 6/1976 Matsuoka et al. .................. 356/328
4,030,828 6/1977 Sonobe et al. ...................... 356/320
4,263,512 4/1981 Saqusa et al. ...................... 356/320

Primary Examiner—F. L. Evans
Attorney, Agent, or Firm—Antonelli, Terry & Wands

[57] ABSTRACT

In a flow injection analysis method of injecting a predetermined amount of a sample into a continuous flow of a carrier solution and introducing a reaction zone of the sample and the carrier solution into a flow cell, signals representative of the respective absorptions of the reaction zone for a plurality of wavelengths are produced when the reaction zone is passing through the flow cell. The signals are subjected to an at least two-wavelength processing or differentiation processing, thereby providing a desired absorbance of a substance of interest for analysis free of the influence of a ghost component.

9 Claims, 12 Drawing Figures

ELIMINATION OF GHOST COMPONENT IN FLOW INJECTION ANALYSIS METHOD

BACKGROUND OF THE INVENTION

The present invention relates to a flow injection analysis (hereinafter referred to simply as FIA) method, and more particularly to the elimination of a ghost component in such a method.

In FIA methods, a predetermined amount of a sample is injected into a continuous flow of a carrier solution so that they react with each other to result in a colored reaction product and are brought into a flow cell for spectrophotometric measurement.

In the conventional FIA method, the existing single-beam or double-beam spectrophotometer has been used so that the time-dependent variation of absorbance occurring in a flow cell is measured for one preselected wavelength. A spectrophotometric measurement system used in the conventional FIA method is shown in FIG. 1. White light energy 31 emitted from a light source 30 impinges on a light dispersion element 32 which in turn serves to separate it into various components at different wavelengths. One separated monochromatic light component 33 having a particular preselected wavelength is passed through a fixed slit 34 into a flow cell 35. The amount of light transmitted through the flow cell 35, i.e. the absorbance is detected by a photodetector 36 and the time-dependent variation of absorbance as shown in FIG. 2A is recorded on a recorder 37 such as an oscillogram. However, this conventional method involves a problem that when measurement is applied to a sample such as sea-water containing salts, ghost peaks giving an increase or decrease in apparent absorbance appear due to the refraction of light, for example, through a convex or concave lens action resulting from a difference in density between both sides of an interface (A or B in FIG. 1) of the sample and a carrier solution (such as distilled water or a reagent) so that the ghost peaks affect the measured value, thereby providing a factor of errors in measurement. FIG. 2B shows a typical example of this kind of ghost peaks which was obtained in the case where a predetermined amount of NaCl solution was injected into a continuous flow of a distilled water as the carrier solution. In such a case, it is usually assumed that no time-dependent variation of optical absorption takes place in the measurement using any wavelength in a visible and ultraviolet range since the distilled water and the NaCl solution are both colorless and clear. In actual practice, however, the ghost peaks as shown in FIG. 2B appear. In the profile shown in FIG. 2B, a negative peak is first developed and thereafter a positive peak appears. A reverse profile will be observed when the NaCl solution is used as a carrier and the water is used as a sample. If the amount of the injected sample is great, the positive and negative peaks are separated from each other. A certain combination of the carrier and the sample will give a more complicated profile. Thus, when the sample contains salts as in sea-water, the obtained time-dependent spectrum will result in a composite form of such spectrums as shown in FIGS. 2A and 2B, so that the ghost peaks constitute a factor of errors affecting the measured absorbance value.

Ghost peaks constituting a factor of errors in the FIA method also appear when a reagent as a carrier solution is colored, when fluid-flow pulsations originating from a carrier feeding pump take place, etc. Though the occurrence of the above-mentioned ghost peaks are known, any effective approach for eliminating the influence thereof has been not proposed.

SUMMARY OF THE INVENTION

An object of the present invention is to provide a spectrophotometric measurement in a FIA method in which the influence of a ghost component is eliminated.

According to a FIA method according to the present invention, the measurement of absorbance using a plurality of wavelengths at a predetermined time rather than the measurement of time-dependent variation in absorbance using a fixed wavelength is carried out. For that purpose, when a reaction zone of a sample and a carrier solution is passing through a flow cell, a light dispersion means and a photodetector means, which are disposed behind the flow cell, are used to produce electric absorption signals representative of the respective absorptions of the reaction zone for a plurality of wavelengths of light within a predetermined wavelength range. Then, the electric absorption signals are arithmetically processed to provide a desired absorbance of a substance of interest for analysis free of the influence of a ghost component.

In one example, there is produced a difference between the value of the absorption signal associated with a wavelength which substantially gives a peak level of absorption and a value related to the value of the absorption signal associated with at least one wavelength which gives a smaller level of absorption.

In another example, the absorption signals are differentiated with respect to wavelength to produce a derivative spectrum.

DESCRIPTION OF THE PREFERRED EMBODIMENTS

Figure 3:
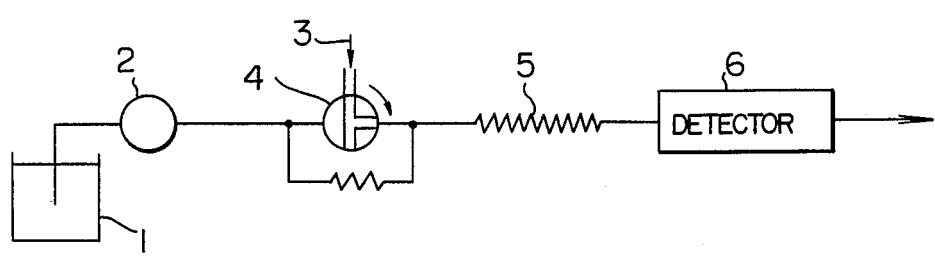
FIG. 3 schematically shows an apparatus to which the present invention is applicable and which is useful for explaining the principle of a FIA method.

First, the principle of a FIA method will be briefly explained referring to FIG. 3. In the figure, a carrier solution 1 such as a reagent is continuously supplied in a constant flow rate by a feeding pump 2. A changeover valve 4 is disposed in the course of a continuous flow of the reagent to inject a predetermined amount of a sample 3 thereinto. The injected sample is mixed and reacts with the reagent in a reaction coil 5, thereby providing a colored appearance. The colored reaction zone or reaction product of the sample and the reagent is introduced into a detector which includes a spectrophotometer and a flow cell for spectrophotometric measurement.

Figure 4:
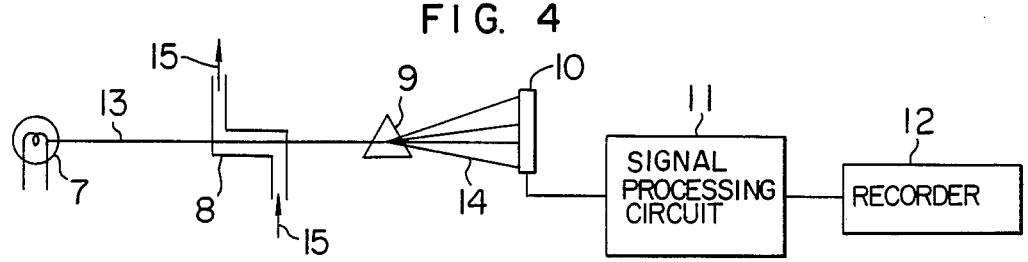
FIG. 4 is a schematic view of a spectrophotometric measurement system used in the FIA method according to the present invention.

A spectrophotometric measurement system used in the present invention is shown in FIG. 4. Referring to the figure, a white light 13 from a light source 7 is passed through a flow cell 8 and thereafter enters a light dispersion element 9 such as a prism or a grating. Monochromatic light components 14 at different wavelengths separated by the dispersion element 9 impinge on an array 10 of photodetectors arranged corresponding to desired wavelengths. Electric output signals from the photodetector array 10 representing the respective absorptions of the flow cell 8 for the corresponding wavelengths are supplied to an arithmetic signal processing circuit 11. The result obtained through the signal processing is recorded by a recorder 12. Reference numeral 15 represents a direction of the flow of the fluid.

Figure 2A:
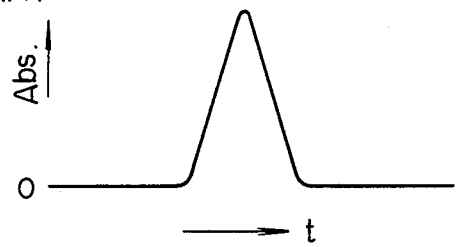
FIG. 2A shows an example of the time-dependent variation of absorbance obtained by the conventional FIA method.
Figure 2B:
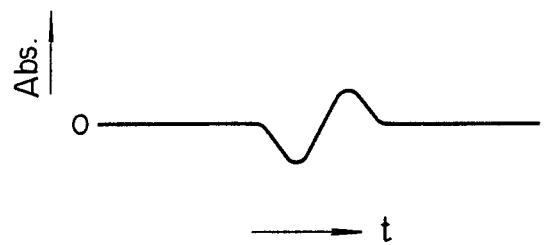
FIG. 2B shows a typical example of ghost peaks produced in the conventional FIA method.

According to an embodiment of the present invention, the output signal of one detector associated with a first wavelength $\lambda_1$ which substantially gives a peak level of absorption and the output signal of another detector associated with a second wavelength $\lambda_2$ which gives a smaller level of absorption or a level at which a substantial absorption is not almost present, are selected to produce a difference therebetween, thereby eliminating the influence of a variation in apparent absorbance resulting from the refraction of light due to a density difference in the flow cell. The first and second wavelengths $\lambda_1$ and $\lambda_2$ or the associated detectors can be preliminarily selected depending the used sample and reagent. This approach can remove a substantial part of the ghost component. The reason is because though ghost peaks as shown in FIG. 2B are superimposed in the case of measuring the time-dependent absorbance for a fixed wavelength, the level of a ghost component in the case of measuring the respective absorbance for a plurality of wavelengths at a fixed time has no great change depending upon wavelength and can be regarded as being almost constant in many cases.

Figure 5:
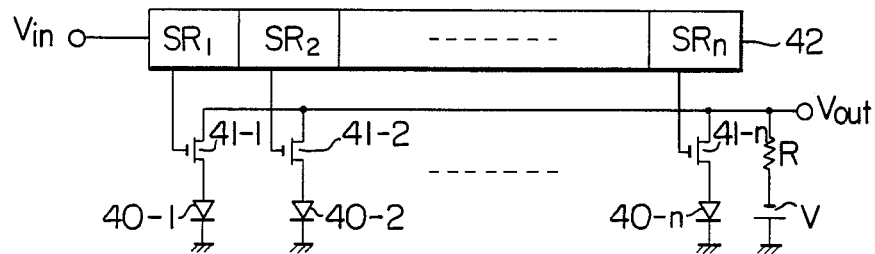
FIG. 5 shows the circuit diagram of an array of photodiodes associated with reading MISFETs which is suitable for use in the present invention.

The above embodiment will be explained by use of FIGS. 5 and 6. Referring to FIG. 5 which shows an example of the detector array 10 suited to the present invention, n photodiodes 40-1 to 40-n are provided which respectively receive the monochromatic light components 14 from the dispersion element 9. The photodiodes 40-1 to 40-n have their cathodes grounded and their anodes connected with the sources of reading MISFETs 41-1 to 41-n respectively. The drains of the FETs are connected in common with one end of a resistor R the other end of which is connected with one end of a voltage source V grounded at the other end. The gates of the FETs 41-1 to 41-n are connected with the outputs of shift registers $SR_1$ to $SR_n$ constituting a scanning circuit 42. With this construction, if the number n of the photodiodes is 200 and the FETs are sequentially fired at a sampling period of 5 $\mu$sec, signals representative of the respective absorptions for wavelengths, for example, 501–700 nm at intervals of 1 nm can be obtained at an output terminal $V_{out}$ for 1000 $\mu$sec. Further explanation is omitted since the details of operation of the circuit shown in FIG. 5 are disclosed in U.S. Pat. No. 4,242,695.

It should be noted that the monochromatic light components from the dispersion element 9 are irradiated onto the photodiodes 40-1 to 40-n at a time to store information of absorptions for the respective wavelengths therein. This timing may be selected to be any instant of time within a period in which the reaction zone of the sample and the carrier solution is passing through the flow cell 8. For example, if one injects a certain dye and a time from the injection of the dye to the appearance of the same dye in the flow cell can be preliminarily determined. Then, the timing of irradiation in the actual measurements can be determined on the basis of the time instant of injection of a sample.

Figure 6:
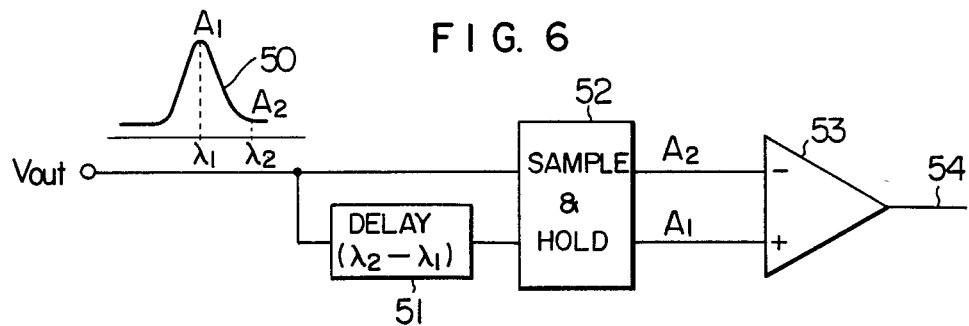
FIG. 6 shows the circuit diagram of a two-wavelength arithmetic processing circuitry as an embodiment of the present invention.

FIG. 6 shows an example of a signal processing circuitry which uses the absorption signals from the output terminal $V_{out}$ of FIG. 5 associated with the plural wavelengths to produce a difference between the values $A_1$ and $A_2$ of the absorption signals associated with two predetermined wavelengths $\lambda_1$ and $\lambda_2$. A signal train 50 from the terminal $V_{out}$ is applied to one input of a sample and hold circuit 52 on one hand and through a delay circuit 51 to another input of the circuit 52 on the other hand. The delay circuit 51 provides a time delay corresponding to the wavelength difference $\lambda_2-\lambda_1$. The sample and hold circuit 52 includes sample and hold sections for the respective inputs, which sections sample and hold those inputs by means of a control pulse corresponding to the wavelength $\lambda_2$. As a result, the sampled and held values $A_2$ and $A_1$ are obtained at the outputs of the sample and hold circuit 52 and supplied to a subtraction circuit 53 which in turn produces a difference of $A_2-A_1$.

Alternatively, the difference of $A_2-A_1$ may be determined from the direct recording of the signal train at the output terminal $V_{out}$ of FIG. 5 on an oscillogram. Also, the difference of $A_2-A_1$ may be determined in such a manner that the signals sequentially produced at the output terminal $V_{out}$ of FIG. 5 are sequentially stored in a memory at addresses corresponding to the respective wavelengths and the stored contents of the memory at two addresses corresponding to the predetermined wavelengths $\lambda_1$ and $\lambda_2$ are read out to produce a difference therebetween. Further, individual photodetectors can be used instead of the photodiode-reading MISFET arrangement of FIG. 5. In such a case, the outputs of those photodetectors may be stored in a memory or only the outputs of two selected photodetectors may be read out for produce a difference therebetween. The used photodetectors may be only two detectors corresponding the desired wavelengths lengths $\lambda_1$ and $\lambda_2$.

Though in the above embodiment the signals associated with two wavelengths are selected and processed, the present invention can employ the processing of the signals associated with three wavelengths. When the ghost peaks shown in FIG. 2B are due to the refraction of light resulting from a density difference, the ghost level in the measurement of absorbance with a plurality of wavelengths has a tendency to increase at shorter wavelengths. In such a case, the three-wavelength processing is preferable.

Figure 7:
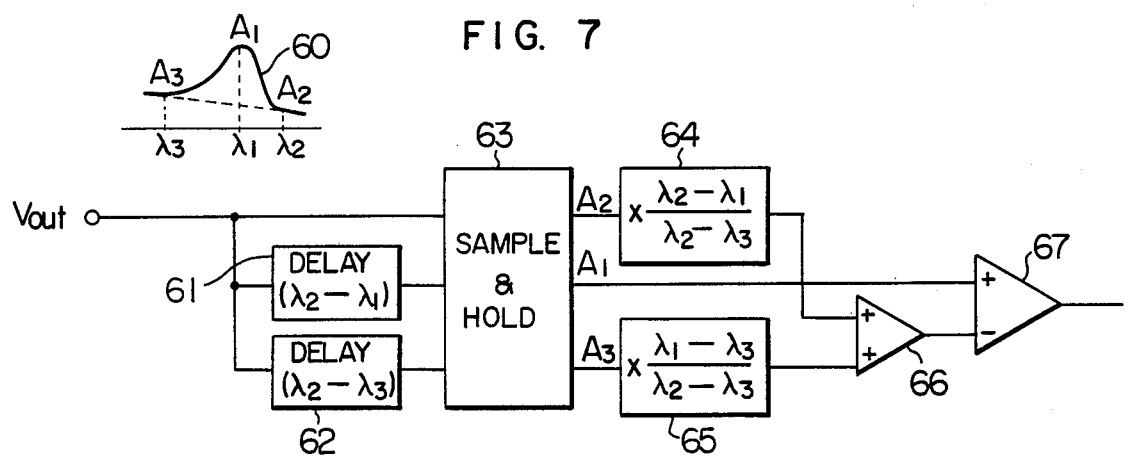
FIG. 7 shows the circuit diagram of a three-wavelength arithmetic processing circuitry as another embodiment of the present invention.

FIG. 7 shows as another embodiment of the present invention an example of an arithmetic processing circuitry suitable for three-wavelength processing. Three wavelengths $\lambda_1$, $\lambda_2$ and $\lambda_3$ satisfying a relation of $\lambda_2 > \lambda_1 > \lambda_3$ are preselected. For a signal train 60 obtained at the output terminal $V_{out}$ of FIG. 5, the processing circuitry serves to produce $$A_1 - \left( \frac{\lambda_2 - \lambda_1}{\lambda_2 - \lambda_3} A_2 + \frac{\lambda_1 - \lambda_3}{\lambda_2 - \lambda_3} A_3 \right).$$

For that purpose, delay circuits 61 and 62 provide time delays corresponding to the wavelength differences $\lambda_2 - \lambda_1$ and $\lambda_2 - \lambda_3$ respectively. Sampled and held values $A_2$ and $A_3$ at first and third outputs of a sample and hold circuit 63 are multiplied with $(\lambda_2 - \lambda_1)/(\lambda_2 - \lambda_3)$ and $(\lambda_1 - \lambda_3)/(\lambda_2 - \lambda_3)$ in multipliers 64 and 65 respectively and are applied to an adder circuit 66 the output of which is supplied to a (−) input of a subtraction circuit 67. A (+) input of the subtraction circuit 67 is applied with the sampled and held value $A_1$ at a second output of the sample and hold circuit 63. The sample and hold circuit 63 perform its sampling and holding operation for each input by means of a control pulse corresponding to the wavelength $\lambda_2$. When the three wavelengths $\lambda_1$, $\lambda_2$ and $\lambda_3$ are selected to satisfy a relation of $\lambda_2 - \lambda_1 = \lambda_1 - \lambda_3$ in the embodiment shown in FIG. 7, it is possible to select the multiplication factors $(\lambda_2 - \lambda_1)/(\lambda_2 - \lambda_3)$ and $(\lambda_1 - \lambda_3)/(\lambda_2 - \lambda_3)$ of the multipliers 64 and 65 to be both $\frac{1}{2}$ irrespective of the selected wavelengths. In this case, the subtraction circuit 67 produces $$A_1 - \frac{A_2 + A_3}{2}.$$

The three-wavelength processing in the present embodiment permits a measurement with higher accuracy in which the influence of a ghost component is further reduced as compared with the aforementioned two-wavelength processing.

The influence of a ghost component can be almost eliminated by the foregoing embodiments. However, it may not be completely eliminated by the two-wavelength or three-wavelength processing in certain cases such as the case where a substance producing a ghost component is not a simple one such as NaCl, the case where a reagent itself is colored and a ghost component resulting therefrom affects the absorption spectrum of a substance of interest for analysis, etc. In such cases, an absorption spectrum is produced and differentiated according to a further embodiment of the present invention to eliminate the influence of such a ghost component. Namely, when a sample having reacted with a reagent is passing through a flow cell, the absorbances in an entire wavelength region or a predetermined wavelength range (for example, $\lambda_1 - 30$ $\mu$m to $\lambda_1 + 30$ $\mu$m) covering the both sides of a wavelength ($\lambda_1$) giving a peak level of absorption by a reaction product are simultaneously produced and are subjected to a differentiation processing.

Figure 8A:
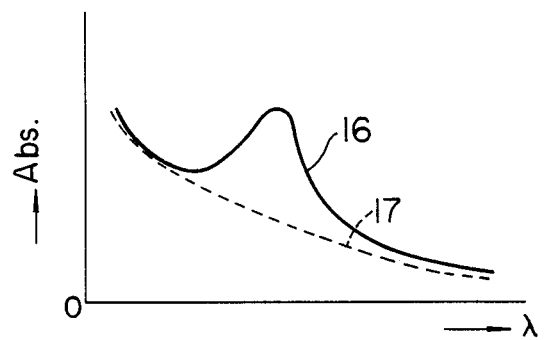
FIGS. 8A to 8C show the examples of measurement for explaining a further embodiment of the present invention.
Figure 8B:
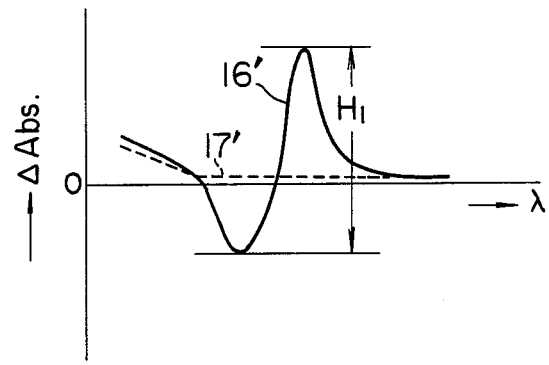
Figure 8C:
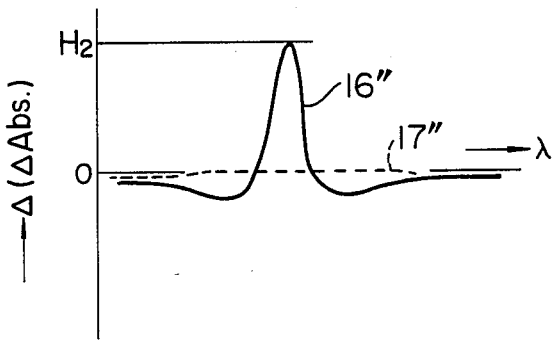

FIGS. 8A to 8C show the examples of measurement for explaining the further embodiment. In FIG. 8A, 16 represents a combined or composite absorption spectrum by a substance under consideration and an undesirable interfering substance, and 17 represents an absorption spectrum of the interfering substance. FIG. 8B shows the 1st order derivative or differential spectra 16' and 17' of the spectra 16 and 17 respectively. FIG. 8C shows the 2nd order derivative or differential spectra 16" and 17" of the spectra 16 and 17 respectively. The differentiation is made in a direction from a longer wavelength to a shorter wavelength. From a difference H1 between maximal and minimal values of the 1st derivative spectrum 16' in FIG. 8B or the height H2 of the maximal value of the 2nd derivative spectrum 16" in FIG. 8C, one can determine an accurate quantity of the substance under consideration which is free of the influence of a ghost component. A derivative higher than the 2nd order will be effective when the absorption spectrum exhibits a more complicated profile than that shown in FIG. 8A.

Figure 9:
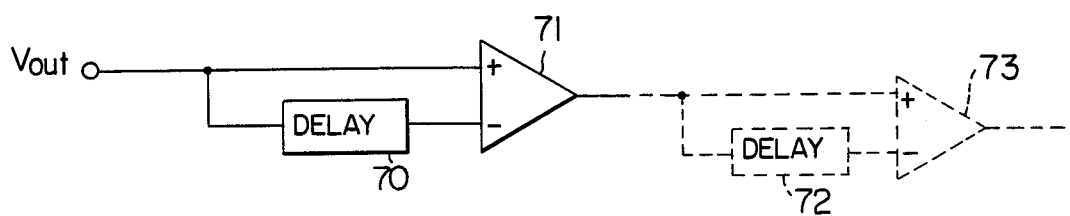
FIG. 9 shows the circuit diagram of a differentiation processing circuitry as the further embodiment.

FIG. 9 shows an example of a differentiation processing circuitry suitable for the above-described further embodiment, which circuitry can use a signal train obtained at the output terminal $V_{out}$ of FIG. 5. The signal train from the terminal $V_{out}$ and a version thereof delayed through a delay circuit 70 by a proper time delay (for example, corresponding to the wavelength interval of 1 or 2 $\mu$m) are supplied to a subtraction circuit 71 which in turn provides a 1st order derivative spectrum at an output thereof. If the output of the subtraction circuit 71 and a delayed version thereof through a second delay citcuit 72 are supplied to a second subtraction circuit 73, the output of the subtraction circuit 73 provides a 2nd derivative spectrum.

The provision of the contruction of FIG. 5 is not essential for producing the derivative spectrum. For example, if individual photodetectors are used and the outputs of those detectors are stored in two parallel channels of a tape in a manner slightly shifted in wavelength from each other, a successive difference between the outputs of the two tape channels can provide a 1st derivative spectrum. If the successive difference signals are stored in two parallel channels of a second tape, a successive difference between the outputs of the second tape channels provides a 2nd derivative spectrum. A computer may be used as a storing means.

Figure 1:
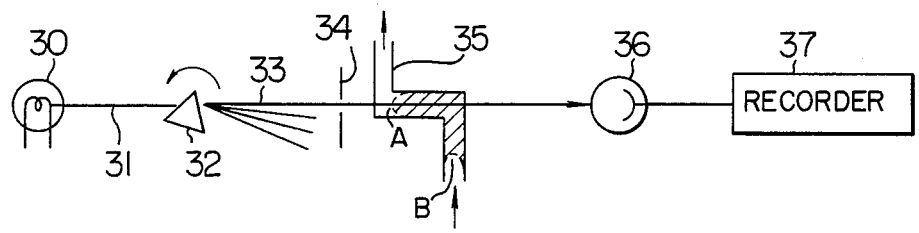
FIG. 1 is a schematic view of a spectrophotometric measurement system used in the conventional FIA method.

Though measurement in plural wavelengths may be possible even in the conventional spectrophotometric measurement system shown in FIG. 1 by mechanically rotating the dispersion element 32, this is actually difficult since a time during when a reaction zone of the sample and the carrier solution passes through the flow cell is very short (e.g. about 1 sec). Further, even if measurement in two wavelengths are possible during a very short time, the absorbances obtained for the two wavelengths are values for different locations of the reaction zone with respect to time which involve different and varying ghost components. Therefore, it is impossible to eliminate the influence of the ghost components from the obtained absorbances.

We claim:
1. A flow injection analysis method comprising:
a first step of injecting a predetermined amount of a sample into a continuous flow of a carrier solution to form a sample zone therein;
a second step of bringing said sample zone into a flow cell which is irradiated with light from a light source, wherein a combination of a light dispersion means and a photodetector means is disposed behind said flow cell for spectrophotometric measurement;

a third step of separating light transmitted through said sample zone in said flow cell into monochromatic light components of different wavelengths by means of said light dispersion means;

a fourth step of directing aaid monochromatic light components onto said photodetector means at a predetermined time to produce electric absorption signals which are representative of the respective absorptions of said sample zone at said predetermined time for a plurality of wavelengths of light within a predetermined wavelength range; and a fifth step of producing a difference between the value of a first one of said absorption signals associated with a preselected first wavelength which substantially gives a peak level of absorption and a value related to the value of a second one of said absorption signals associated with at least one preselected second wavelength which gives a smaller level of absorption.

2. A flow injection analysis method according to claim 1, wherein in said fifth step, one wavelength is selected as said second wavelength and the difference of $A_1 - A_2$ is produced, $A_1$ and $A_2$ being said first and second absorption signal values respectively.

3. A flow injection analysis method according to claim 1, wherein in said fifth step, two wavelengths $\lambda_2$ and $\lambda_3$ satisfying a relation of $\lambda_2 > \lambda_1 > \lambda_3$ and having their associated second absorption signal values $A_2$ and $A_3$ respectively, $\lambda_1$ being said first wavelength having the associated first absorption signal value $A_1$, are selected as said second wavelength and the difference of $$A_1 - \left( \frac{\lambda_2 - \lambda_1}{\lambda_2 - \lambda_3} A_2 + \frac{\lambda_1 - \lambda_3}{\lambda_2 - \lambda_3} A_3 \right)$$

is produced.

4. A flow injection analysis method according to claim 3, wherein said second wavelengths $\lambda_2$ and $\lambda_3$ satisfy a relation of $\lambda_2 - \lambda_1 = \lambda_1 - \lambda_3$ and the difference $$A_1 - \frac{A_2 + A_3}{2}$$

is produced.

5. A flow injection analysis method according to claim 1, wherein said carrier solution includes a reagent and said sample zone formed at said first step is a zone where the injected sample reacts with the reagent.

6. A flow injection analysis method comprising:

a first step of injecting a predetermined amount of a sample into a continuous flow of a carrier solution to form a sample zone therein;

a second step of bringing said sample zone into a flow cell which is irradiated with light from a light source, wherein a combination of a light dispersion means and a photodetector means is disposed behind said flow cell for spectrophotometric measurement;

a third step of separating light transmitted through said sample zone in said flow cell into monochromatic light components of different wavelengths by means of said light dispersion means;

a fourth step of directing said monochromatic light components onto said photodetector means at a predetermined time to produce electric absorption signals which are representative of the respective absorptions of said sample zone at a predetermined time for a plurality of wavelengths of light within a predetermined wavelength range; and a fifth step of differentiating said absorption signals with respect to wavelength to produce a derivative spectrum.

7. A flow injection analysis method according to claim 6, wherein said carrier solution includes a reagent and said sample zone formed at said first step is a zone where the injected sample reacts with the reagent.

8. A flow injection analysis method according to claim 6, wherein the differentiation in said fifth step is carried out once to produce a 1st order derivative spectrum.

9. A flow injection analysis method according to claim 6, wherein the differentiation in said fifth step is carried out twice to produce a 2nd order derivative spectrum.

* * * * *